(12) United States Patent
Cavazza

(10) Patent No.: US 8,853,229 B2
(45) Date of Patent: Oct. 7, 2014

(54) COMPOSITION CONTAINING STATINS AND OMEGA-3 FATTY ACIDS

(75) Inventor: Claudio Cavazza, Pomezia (IT)

(73) Assignee: Sigma-Tau Industrie Farmaceutiche Riunite S.p.A., Rome (IT)

( * ) Notice: Subject to any disclaimer, the term of this patent is extended or adjusted under 35 U.S.C. 154(b) by 1319 days.

(21) Appl. No.: 11/632,953

(22) PCT Filed: Jul. 19, 2005

(86) PCT No.: PCT/IT2005/000414
§ 371 (c)(1),
(2), (4) Date: Mar. 30, 2007

(87) PCT Pub. No.: WO2006/013602
PCT Pub. Date: Feb. 9, 2006

(65) Prior Publication Data
US 2008/0089876 A1 Apr. 17, 2008

(30) Foreign Application Priority Data
Aug. 3, 2004 (IT) .............................. RM2004A0395

(51) Int. Cl.
| | |
|---|---|
| A61K 31/505 | (2006.01) |
| A61K 31/202 | (2006.01) |
| A61K 33/30 | (2006.01) |
| A61K 31/4433 | (2006.01) |
| A61K 31/366 | (2006.01) |
| A61K 33/04 | (2006.01) |
| A61K 31/175 | (2006.01) |
| A61K 31/045 | (2006.01) |
| A61K 45/06 | (2006.01) |
| A61K 31/122 | (2006.01) |
| A61K 31/05 | (2006.01) |

(52) U.S. Cl.
CPC .............. *A61K 45/06* (2013.01); *A61K 31/202* (2013.01); *A61K 33/30* (2013.01); *A61K 31/4433* (2013.01); *A61K 31/366* (2013.01); *A61K 33/04* (2013.01); *A61K 31/175* (2013.01); *A61K 31/045* (2013.01); *A61K 31/122* (2013.01); *A61K 31/05* (2013.01)
USPC ........................... 514/275; 514/419; 514/460

(58) Field of Classification Search
None
See application file for complete search history.

(56) References Cited

U.S. PATENT DOCUMENTS

| | | | | |
|---|---|---|---|---|
| 6,063,820 A | * | 5/2000 | Cavazza | 514/739 |
| 6,964,969 B2 | * | 11/2005 | McCleary | 514/283 |
| 2002/0182585 A1 | | 12/2002 | Kindness et al. | |
| 2003/0175372 A1 | | 9/2003 | Liu | |
| 2003/0228393 A1 | * | 12/2003 | Zhao | 426/74 |
| 2004/0018248 A1 | * | 1/2004 | Bendich | 424/682 |
| 2005/0002992 A1 | * | 1/2005 | McCleary et al. | 424/439 |
| 2005/0256178 A1 | * | 11/2005 | Eggersdorfer et al. | 514/393 |

FOREIGN PATENT DOCUMENTS

| | | |
|---|---|---|
| CN | 1 126 092 A | 7/1996 |
| CN | 1 222 380 A | 7/1999 |
| WO | 02/43659 A2 | 6/2002 |
| WO | 2004/028469 A2 | 4/2004 |
| WO | 2004/041257 A2 | 5/2004 |

OTHER PUBLICATIONS

International Search Report of PCT/IT2005/000414, mailed Nov. 28, 2005.
Miura Daiki et al., "Hypolipidemic action of dietary resveratrol, a phytoalexin in grapes and red wine, in hepatoma-bearing rats", Life Sciences, vol. 73, No. 11, Aug. 1, 2003, pp. 1393-1400, XP009056731.
Database WPI, Section Ch, Week 199749, Derwent Publication Ltd., Class B04, AN 1997-527069, XP002354106.
Database WPI, Section Ch, Week 199946, Derwent Publications Ltd., Class B04, AN 1999-541120, XP002354107.

* cited by examiner

*Primary Examiner* — Lisa J Hobbs
(74) *Attorney, Agent, or Firm* — Lucas & Mercanti, LLP

(57) ABSTRACT

A combination is described comprising at least one omega-3 fatty acid, optionally esterified or salified, at least one statin, Coenzyme Q10, resveratrol, at least one policosanol, pantethine, selenium, and zinc. This combination is endowed with a synergistic effect and is useful in the treatment of disease forms due to insulin resistance and in cardiovascular diseases.

23 Claims, No Drawings

COMPOSITION CONTAINING STATINS AND OMEGA-3 FATTY ACIDS

This application is the US national phase of international application PCT/IT2005/000414, filed 19 Jul. 2005, which designated the U.S. and claims priority of IT RM2004A000395, filed 3 Aug. 2004, the entire contents of each of which are hereby incorporated by reference.

The present invention relates to a combination of active ingredients and to compositions containing this combination in medical use and in the preparation of medicaments useful for the treatment of type 2 diabetes and cardiovascular diseases.

Diabetes is a widespread disease throughout the world and is associated with major clinical complications involving the microvascular district, such as diabetic retinopathy, diabetic neuropathy and nephropathy, and the macrovascular district, such as atherosclerosis, peripheral vasculopathies, myocardial infarct and stroke.

Insulin resistance, which characterises type 2 diabetes and its micro- and macrovascular complications is also involved in syndrome X, poly-cystic ovary syndrome, obesity, hypertension, hyperlipidaemias and hypercholesterolaemias (*J. Am. Osteopath. Assoc.,* 2000 October; 100(10):621-34; *Jama,* 2002 Nov., 27;288(20):2579-88).

It is known that hyperlipidaemias, hypercholesterolaemias and hyper-tension play a decisive role in the onset of coronary heart disease (CHD).

It is also known that an increase in glycosylation of proteins is involved in the above-mentioned complications of diabetes (*Diabetologia* 2001 February; 44(2):129-46).

Said complications constitute a serious threat to the life and well-being of the individual.

Various clinical forms of diabetic disease are known, the most common being type 2 and type 1 diabetes. Type 2 diabetes is characterised by reduced sensitivity to the action of insulin (insulin resistance) and gives rise to an increase in insulin levels in the body in an attempt to compensate for this deficiency and to a consequent increase in glucose levels. Numerous reports have confirmed the involvement of insulin resistance in many disease conditions in addition to type 2 diabetes itself, such as dyslipidaemia, obesity, arterial hypertension and certain macrovascular and microvascular manifestations characteristic of diabetic disease itself. The combination of insulin resistance and obesity, hypertension and dyslipidaemia is known as Syndrome X.

Drugs used for many years such as the biguanides and sulphonylurea drugs are available on the market for the treatment of type 2 diabetes. Many of these, such as, for example, methformin, present gastrointestinal disorders, danger of acidosis in conditions of renal, cardiac, hepatic, pulmonary insufficiency, etc., as side effects. The sulphonylureas have episodes of hypoglycaemia as their possible side effects. Drugs recently introduced onto the market are the thiazolidinediones, whose side effects such as liver toxicity, increased LDL cholesterol, weight gain and oedema have given cause for concern.

Hyperlipidaemia is a serious aspect of diabetic disease, constituting, together with the hypertension which is often present, a risk factor for atherosclerosis and for cardiovascular disease which is the primary cause of death in diabetes.

Cardiovascular disease is recognised as the primary cause of death in the industrialised countries with a high standard of living.

The social cost is enormous, both in terms of disability and invalidity of subjects suffering from it, and in terms of the actual cost of health facilities and insurance.

Dyslipidaemia is often associated, also as a consequence, with diabetes.

In WO 02/43659 a combination of statin, docosahexanoic acid, vitamins E, C B6 and B12, folic acid and calcium is described to reduce the risk factors for cardiovascular disease, such as hypercholesterolaemia and hypertension. In this document there is never any mention of insulin resistance.

Ever increasing attention is being devoted to the so-called risk factors recognised as underlying these diseases, and there is still a perceived need for a medicament capable of acting on the various sources of this pathological picture, without, at the same time, being associated with severe side effects, which, as in the case of certain antidiabetic drugs, may even make it necessary to discontinue the therapy.

SUMMARY OF THE INVENTION

It has now surprisingly been found that a certain combination of substances, known for their specific pharmacological actions, is particularly indicated for the treatment of insulin resistance, and of the pathological aspects related to it, as well as of cardiovascular diseases. The combination according to the invention comprises essentially at least one omega-3 fatty acid, optionally esterified or salified, at least one statin, Coenzyme Q10, resveratrol, at least one policosanol, pantethine, selenium and zinc.

The unique combination according to the present invention exerts a surprising effect on insulin resistance, which is not predictable on the basis of our knowledge of the individual components thereof, and, in any event, their combination leads to an unexpected synergistic effect.

The advantage of having such a combination is therefore evident to experts in the field. It is possible, in fact, to treat insulin resistance, and the pathological forms related to it, particularly as regards the implications of abnormal lipid status, and, at the same time, the complications or risks affecting the cardiocirculatory system.

The combination according to the present invention can also be used for the treatment of cardiovascular diseases, without there necessarily being any need to treat insulin resistance.

Therefore, one object of the present invention is a combination comprising at least one omega-3 fatty acid, optionally esterified or salified, at least one statin, Coenzyme Q10, resveratrol, at least one policosanol, pantethine, selenium, and zinc.

The combination according to the invention can also comprise other useful elements, without this substantially impairing the activity.

Another object of the present invention is a pharmaceutical composition containing the above-mentioned combination, optionally in a mixture with one or more pharmaceutically acceptable vehicles or excipients.

The combination according to the present invention can also be formulated as a food supplement, which constitutes a further object of the invention.

Other objects of the present invention are various uses of the above-mentioned combination as a medicament, in particular for the preparation of a medicament for the treatment of insulin resistance and type 2 diabetes, with antilipaemic action and a protective action on the cardiovascular system.

In particular, the present invention provides for the use of the above-mentioned combination for the preparation of a medicament useful for the treatment of diseases involving insulin resistance, such as type 2 diabetes, Syndrome X, polycystic ovary syndrome, obesity, hypertension, hperlipidaemias and hypercholesterolaemias.

The medicament according to the invention can be used to treat the individual disease states or to exert a preventive or protective action against them, or to treat a complex pathological picture that includes one or more of the therapeutic aspects seen above. For example, a medicament with a combined action for the treatment of type 2 diabetes and insulin resistance and an antilipaemic and protective action on the cardiovascular system, particularly in certain severe forms of type 2 diabetes associated with obesity.

DETAILED DESCRIPTION OF THE INVENTION

The combination according to the present invention consists essentially of active ingredients which are known in the medical field and already used in clinical practice. Therefore, they are very easy to procure, inasmuch as they are products which have been on the market for some time and are of a grade suitable for human or animal administration.

The statins are a known class of drugs used for lowering cholesterol levels. Statins are available on the market or can be prepared according to known methods described in the literature.

Any statin is suitable for the purposes of the present invention. Examples of statins are simvastatin, lovastatin, fluvastatin, pravastatin, atorvastatin, cerivastatin and rosuvastatin. Among these, the one preferred is simvastatin.

According to the present invention, it is also possible to combine a number of statins, depending on their pharmacological characteristics and on the basis of the common knowledge of experts in the field.

The omega-3 fatty acids are known for their triglyceride-lowering effects and for their effects in raising the levels of high-density lipoproteins (HDL). These fatty acids can be obtained by synthesis or, preferably, from fish oil. In that case, it is possible to use various mixtures of omega-3 fatty acids depending on their characteristics. Preferably, the omega-3 fatty acids are the long-chain ones (from 20 to 22 carbon atoms). The ones most preferred are 5,8,11,14,17-eicosapentanoic acid (EPA) and cis 0,13,16,19-docosahexanoic acid (DHA). In a preferred embodiment of the invention, the omega-5 fatty acid is cis 4,7,10,13,16,19-docosahexanoic acid (DHA), most preferably in a ratio of 1:1. These omega-3 fatty acids can optionally be esterified or salified to pharmaceutically acceptable derivatives, with alcohols or bases, respectively. The omega-3 fatty acids, or their esters or salts, alone or in mixtures thereof, can be procured on the market, or can be prepared by known methods. The mixtures can be specifically formulated for the combination according to the invention.

Coenzyme Q10 is now so well known in its human use that it requires no particular explanation and the substance is available on the market. Experts in the field can refer to the patent documents filed by the present applicant, where this substance is amply described.

Similar considerations also apply to resveratrol.

The policosanols are long-chain aliphatic alcohols. Examples of policosanols are triacontanol, hexacosanol, hexacontanol, ecocontanol, tetracosanol, dotriacontanol, and tetracontanol. The policosonal can be present as such or in the form of an extract from natural products that contain it, e.g. wheat or rice germs, the waxy cuticle of sugar cane, or *Ginkgo biloba* leaves. See, for example, WO 99/06039.

Pantethine is used on compositions for hair cosmetics and also in compositions for the treatment of dyslipidaemias, as described, for example, in WO 2004/041257. It is therefore a well-known compound available to the expert in the field.

Selenium and zinc are commonly used in food supplements, as described in several patents, e.g. EP 0 797 993 and U.S. Pat. No. 6,602,512.

As already mentioned, the individual components have long been used in human subjects, and therefore their pharmaco-toxicological profiles are known.

This implies that, apart from the consideration of the synergistic effect demonstrated here below, the dosages and ratios of the individual components can be determined by the expert in the field with normal preclinical and clinical trials, or with the usual considerations regarding the formulation of a dietetic product.

The amounts of the individual compounds advised for the preparation of a pharmaceutical composition for human use are the following.

Omega-3 fatty acid: from 500 mg to 2 g/day, preferably 1 g/day;

Simvastatin; from 10 mg to 40 mg/day, preferably 10 mg/day;

Coenzyme Q10: from 5 mg to 50 mg/day, preferably 10 mg/day;

Resveratrol: from 1 mg to 5 mg/day, preferably 2.5 mg/day;

Policosanols: hexacosanol: from 5 mg to 15 mg/day, preferably 10 mg/day;

Pantethine: from 10 mg to 30 mg/day, preferably 20 mg/day;

Selenium: from 25 µg to 75 µg/day, preferably 50 µg/day;

Zinc: from 5 mg to 15 mg/day, preferably 10 mg/day.

The pharmaceutical composition can have a unitary form, in which the active ingredients are present in a single pharmaceutical form (tablet, sachet, capsule, vial) or the active ingredients can be administered in a coordinated sequential manner. In the latter case, the pharmaceutical composition can be formulated, supplying the components in separate containers, accompanied by instructions for their sequential administration.

The compositions covered by the present invention are entirely conventional and are obtained with methods that are common practice in the pharmaceutical industry. According to the administration route opted for, the compositions will be in solid or liquid form, suitable for oral, parenteral or intravenous administration. The compositions according to the present invention contain, along with the active ingredient, at least one pharmaceutically acceptable vehicle or excipient. Particularly useful may be formulation adjuvants such as, for example, solubilising agents, dispersing agents, suspension agents and emulsifying agents. A general reference work is *Remington's Pharmaceutical Sciences Handbook*, latest edition.

The following examples further illustrate the invention.

EXAMPLE 1

Antidiabetic and Serum Lipid-Lowering Activity in db/db Mice

Mutations in laboratory animals have made it possible to develop models that present non-insulin-dependent diabetes associated with obesity, hyperlipidaemia and insulin resistance and that enable us to test the efficacy of new antidiabetic compounds (Reed and Scribner, Diabetes, obesity and metabolism 1: 75-86, 1999).

A much used genetically diabetic mouse model is the C57BL/KsJ db/db mouse.

The genetic basis of this model is a defect in the leptin receptor gene which gives rise to leptin resistance and leads to hyperphagia, obesity, hyperinsulinaemia and insulin resistance, with subsequent symptoms of insufficient insulin secretion and hyperglycaemia (Kodama et al., Diabetologia 37: 739-744, 1994; Chen et al., Cell 84: 491-495, 1996). Since hyperglycaemia is accompanied by obesity and insulin resistance, the db/db mouse has characteristics that are close to those of type 2 diabetes in man and is useful for assaying insulin-sensitising compounds.

The C57BL/KsJ db/db mice used in the experiments were supplied by Jackson Lab (via Ch. River). After 10 days of acclimatisation in standard conditions (22±2° C.; 55±15% humidity; 15-20 air changes/hour; 12 hour light-darkness cycle with light from 7 a.m. to 7 p.m.) on a standard 4 RF21 diet (Mucedola), blood samples were taken in post-absorption conditions (fasting from 8.30 a.m. to 4.30 p.m.) from the caudal vein with the aid of a Jelco 22G catheter (Johnson and Johnson). Glucose, insulin, triglyceride, cholesterol, free fatty acid and urea levels were checked in the plasma to ensure well-matched distribution of the mice in the treatment groups.

At the start of treatment, the body weight of the animals was checked and monitoring of the animals' consumption of water and feed was scheduled.

The mice were divided into groups and treated orally twice daily with:

Omega-3 fatty acid (EPA+DHA 1:1) 200 mg/kg;
Simvastatin 100 mg/kg;
Omega-3 fatty acid (200 mg/kg)+simvastatin (100 mg/kg);
Omega-3 fatty acid (200 mg/kg)+simvastatin (100 mg/kg); Coenzyme Q10 (50 mg/kg)+resveratrol (5 mg/kg)+policosanols (hexacosanol 25 mg/kg)+pantethine (100 mg/kg+selenium (0.5 µg/kg)+zinc (2.5 mg/kg).

In the course of the experiment, serum glucose levels, glucose tolerance (OGTT), a number of lipid status variables and weight gain were monitored.

The combination according to the invention was capable of lowering serum glucose levels in the feeding condition (Table 1); in the post-absorption condition (Table 2); and in the fasting condition (Table 3); and capable of improving glucose tolerance (Table 4), and of reducing the levels of fructosamine, an indicator of protein glycosylation (Table 5) which, as mentioned above, plays an important role in the development of the micro- and macrovascular complications of diabetes.

The combination according to the invention also shows good ability to reduce serum triglyceride levels (Table 6) and to increase HDL-cholesterol levels (Table 7).

An increase in HDL-cholesterol values constitutes an indicator of a reduced risk of atherosclerosis and of cardiovascular complications such as atherosclerosis and infarct.

TABLE 1

| Compound | Glucose mg/dl | % Variation | P Student's t-test) |
|---|---|---|---|
| Control | 487 ± 25 | | |
| Simvastatin | 450 ± 21 | −7.6 | NS |
| Omega-3 | 466 ± 28 | −4.3 | NS |

TABLE 1-continued

| Compound | Glucose mg/dl | % Variation | P Student's t-test) |
|---|---|---|---|
| Omega-S + simvastatin | 403 ± 34 | −17.2 | NS |
| Omega-3 (200 mg/kg) + simvastatin (100 mg/kg) + Coenzyme Q10 (50 mg/kg) + resveratrol (5 mg/kg) + hexacosanol 25 mg/kg) + pantethine (100 mg/kg + selenium (0.5 µg/kg) + zinc (2.5 mg/kg) | 303 ± 16 | −37.8 | P < 0.001 vs control |

Number of animals per group: 6.
Blood glucose levels of db/db mice, treated orally twice daily for 12 days with the compounds and at the doses indicated in the table. Sample in feeding condition, approximately 15 hours after the last treatment.
Mean values ± S.E. and variation (%) vs control.

TABLE 2

| Compound | Glucose mg/dl | % Variation | P Student's t-test) |
|---|---|---|---|
| Control | 414 ± 11 | | |
| Simvastatin | 419 ± 33 | 1.2 | NS |
| Omega-3 | 421 ± 30 | 1.6 | NS |
| Omega-3 + simvastatin | 409 ± 11 | −1.2 | NS |
| Omega-3 (200 mg/kg) + simvastatin (100 mg/kg); + Coenzyme Q10 (50 mg/kg) + resveratrol (5 mg/kg) + hexacosanol 25 mg/kg) + pantethine (100 mg/kg + selenium (0.5 µg/kg) + zinc (2.5 mg/kg) | 216 ± 16 | −47.8 | P < 0.001 vs control |

Number of animals per group: 6.
Blood glucose levels of db/db mice, treated orally twice daily for 12 days with the compounds and at the doses indicated in the table. Sample in post-absorption condition (fasting from 9 a.m. to 5 p.m.) and 8 hours after the last treatment.
Mean values ± S.E. and variation (%) vs control.

TABLE 3

| Compound | Glucose mg/dl | % Variation | P Student's t-test) |
|---|---|---|---|
| Control | 344 ± 35 | | |
| Simvastatin | 325 ± 27 | −5.5 | NS |
| Omega-3 | 314 ± 21 | −8.7 | NS |
| Omega-3 + simvastatin | 384 ± 20 | 11.6 | NS |
| Omega-3 (200 mg/kg) + simvastatin (100 mg/kg); + Coenzyme Q10 (50 mg/kg) + resveratrol (5 mg/kg) + hexacosanol 25 mg/kg) + pantethine (100 mg/kg + selenium (0.5 µg/kg) + zinc (2.5 mg/kg) | 144 ± 3 | −58.0 | P < 0.001 vs control |

Number of animals per group: 6.
Blood glucose levels of db/db mice, treated orally twice daily for 18 days with the compounds and at the doses indicated in the table. Sample in mice fasted for 18 hours and 5 hours after the last treatment.
Mean values ± S.E. and variation (%) vs control.

TABLE 4

| Compound | AUC Glucose u.a. | % Variation | P Student's t-test |
|---|---|---|---|
| Control | 51182 ± 2392 | | |
| Simvastatin | 48174 ± 3555 | −5.9 | NS |
| Omega-3 | 46476 ± 1827 | −9.2 | NS |
| Omega-3 + simvastatin | 45192 ± 1546 | −11.7 | NS |
| Omega-3 (200 mg/kg) + simvastatin (100 mg/kg); + Coenzyme Q10 (50 mg/kg) + | 24527 ± 889 | −52.1 | P < 0.001 vs control |

TABLE 4-continued

| Compound | AUC Glucose u.a. | % Variation | P Student's t-test |
|---|---|---|---|
| resveratrol (5 mg/kg) + hexacosanol 25 mg/kg) + pantethine (100 mg/kg + selenium (0.5 µg/kg) + zinc (2.5 mg/kg) | | | |

Number of animals: 6.
Area under the curve (AUC) of the OGTT in the blood of db/db mice, treated orally twice daily for 18 days with the compounds and at the doses indicated in the table. OGTT test (glucose 3 g/kg) in mice fasted for 18 hours and 5 hours after the last treatment.
Mean values ± S.E. and variation (%) vs control.

TABLE 5

| Compund | Fructosamine mM | % Variation | P Student's t-test |
|---|---|---|---|
| Control | 0.80 ± 0.03 | | |
| Simvastatin | 0.78 ± 0.12 | −2.5 | NS |
| Omega-3 | 0.81 ± 0.04 | 1.3 | NS |
| Omega-3 + simvastatin | 0.82 ± 0.02 | 2.5 | NS |
| Omega-3 (200 mg/kg) + simvastatin (100 mg/kg) + Coenzyme Q10 (50 mg/kg) + resveratrol (5 mg/kg) + hexacosanol 25 mg/kg) + pantethine (100 mg/kg + selenium (0.5 µg/kg) + zinc (2.5 mg/kg) | 0.41 ± 0.04 | −48.8 | P < 0.001 vs control |

Number of animals per group: 6.
Plasma fructosamine levels of db/db mice, treated orally twice daily for 25 days with the compounds and at the doses indicated in the table. Sample in post-absorption condition (fasting from 9 a.m. to 4.30 p.m.) and 7.30 hours after the last treatment.
Mean values ± S.E. and variation (%) vs control.

TABLE 6

| Compound | Triglycerides mg/dl | Variation | P Student's t-test |
|---|---|---|---|
| Control | 95.4 ± 6.2 | | |
| Simvastatin | 79.7 ± 5.1 | −16.5 | NS |
| Omega-3 | 88.3 ± 10.7 | −7.4 | NS |
| Omega-3 + simvastatin | 73.5 ± 4.5 | −22.9 | 0.05 vs control |
| Omega-3 (200 mg/kg) + simvastatin (100 mg/kg) + Coenzyme Q10 (50 mg/kg) + resveratrol (5 mg/kg) + hexacosanol 25 mg/kg) + pantethine (100 mg/kg + selenium (0.5 µg/kg) + zinc (2.5 mg/kg) | 45.3 ± 2.3 | −52.5 | 0.001 vs control |

Number of animals per group: 6.
Plasma triglyceride levels of db/db mice, treated orally twice daily for 25 days with the compounds and at the doses indicated in the table. Sample in post-absorption condition (fasting from 9 a.m. to 4.30 p.m.) and 7.30 hours after the last treatment.
Mean values ± S.E. and variation (%) vs control.

TABLE 7

| Compound | HDL-cholesterol mg/dl | % Variation | P Student's t-test |
|---|---|---|---|
| Control | 82.0 ± 5.1 | | |
| Simvastatin | 72.4 ± 4.6 | −11.7 | NS |
| Omega-3 | 74.8 ± 3.8 | −8.8 | NS |
| Omega-3 + simva-statin | 78.4 ± 4.1 | −4.4 | NS |
| Omega-3 (200 mg/kg) + simvastatin | 98.0 ± 3.5 | 19.5 | 0.05 |

TABLE 7-continued

| Compound | HDL-cholesterol mg/dl | % Variation | P Student's t-test |
|---|---|---|---|
| (100 mg/kg); + Coenzyme Q10 (50 mg/kg) + resveratrol (5 mg/kg) + hexacosanol 25 mg/kg) + pantethine (100 mg/kg + selenium (0.5 µg/kg) + zinc (2.5 mg/kg) | | | vs control |

Plasma HDL-cholesterol levels of db/db mice, treated orally twice daily for 25 days with the compounds and at the doses indicated in the table. Sample in post-absorption conditions (fasting from 9 a.m. to 4.30 p.m.) and 7.30 hours after the last treatment.
Mean values ± S.E. and variation (%) vs control.

The results reported above clearly demonstrate the unexpected synergism of the combination according to the present invention, contrary to what was expected on the basis of the individual components, or even of the combination of simvastatin and omega-3 fatty acids.

The invention claimed is:

1. A method for the treatment of type 2 diabetes in a subject in need thereof, comprising
    administering a dosage consisting essentially of the following components:
    an omega-3 fatty acid selected from the group consisting essentially of cis 5,8,11,14,17-eicosapentanoic acid (EPA) and cis 4,7,10,13,16,19-docosahexanoic acid (DHA), one of their esters or pharmaceutically acceptable salts or mixture thereof, a statin, Coenzyme Q10, resveratrol, a policosanol, pantethine, selenium and zinc, to said subject suffering from type 2 diabetes, whereby said dosage lowers serum glucose levels in feeding and fasting conditions after administration; and
    treating said type 2 diabetes in said subject in need.

2. The method according to claim 1, in which the statin is selected from the group consisting of simvastatin, lovastatin, fluvastatin, pravastatin, atorvastatin, cerivastatin and rosuvastatin.

3. The method according to claim 1, in which the omega-3 fatty acid is long-chain.

4. The method according to claim 1, in which the cis 5,8,11,14,17-eicosapentanoic acid (EPA) and cis 4,7,10,13,16,19-docosahexanoic acid (DHA), one of their esters or pharmaceutically acceptable salts are in a ratio of 1:1.

5. The method according to claim 1, in which the policosanol is selected from the group consisting of triacontanol, hexacosanol, hexacontanol, ecocontanol, tetracosanol, dotriacontanol and tetracontanol.

6. The method according to claim 5, in which the policosanol is present as such or in the form of an extract from natural products that contain it.

7. The method according to claim 6, in which the natural product is selected from the group consisting of wheat or rice germs, the waxy cuticle of sugar cane and *Ginkgo biloba* leaves.

8. The method accordin to claim 1, in which said components of the dosage are optionally in a mixture with at least one pharmaceutically acceptable vehicle or excipient.

9. The method according to claim 8, wherein said dosage includes the following components:
    a. omega-3 fatty acid: from 500 mg to 2 g/day;
    b. simvastatin: from 10 mg to 40 mg/day;
    c. Coenzyme Q10: from 5 mg to 50 mg/day;
    d. resveratrol: from 1 mg to 5 mg/day;
    e. policosanols: hexacosanol: from 5 mg to 15 mg/day;
    f. pantethine: from 10 mg to 30 mg/day;
    g. selenium: from 25 µg to 75 µg/day; and
    h. zinc: from 5 mg to 15 mg/day.

10. The method according to claim 1, in which the components of the dosage are administered in unitary form, or in coordinated, sequential form.

11. The method according to claim 1, in which said dosage is administered in the form of a pharmaceutical composition or a food supplement.

12. A method for the treatment of diseases involving insulin resistance in as subject in need thereof, comprising
administering a dosage-consisting essentially of the following components:
an omega-3 fatty acid selected from the group consisting of cis 5,8,11,14,17-eicosapentanoic acid (EPA) and cis 4,7,10,13,16,19-docosahexanoic acid (DHA), one of their esters or pharmaceutically acceptable salts or mixtures thereof, a statin, Coenzyme Q10, resveratrol, a policosanol, pantethine, selenium, and zinc to said subject suffering from insulin resistance whereby said dosage lowers serum glucose levels in feeding and fasting conditions after administration: and
treating said diseases in insulin resistance.

13. The method according to claim 12, in which the statin is selected from the group consisting of simvastatin, lovastatin, fluvastatin, pravastatin, atorvastatin, cerivistatin, and rosuvastatin.

14. The method according to claim 12, in which the omega-3 fatty acid is long-chain.

15. The method according to claim 12, in which the cis 5,8,11,14,17-eicosapentanoic acid (EPA) and cis 4,7,10,13,16,19-docosahexanoic acid (DHA), one of their esters or pharmaceutically acceptable salts are in a ratio of 1:1.

16. The method according to claim 12, in which the policosanol is selected from the group consisting of triacontanol, hexacosanol, hexacontanol, ecocontanol, tetracosanol, dotriacontanol and tetracontanol.

17. The method according to claim 16, in which the policosanol is present as such or in the form of an extract from natural products that contain it.

18. The method according to claim 17, in which the natural product is selected from the group consisting of wheat or rice germs, the waxy cuticle of sugar cane and *Ginkgo biloba* leaves.

19. The method according to claim 12, in which said components of the dosage are optionally in a mixture with at least one pharmaceutically acceptable vehicle or excipient.

20. The method according to claim 19, in which said dosage includes the components:
a. omega-3 fatty acid: from 500 mg to 2 g/day;
b. simvastatin: from 10 mg to 40 mg/day;
c. Coenzyme Q10: from 5 mg to 50 mg/day;
d. resveratrol: from 1 mg to 5 mg/day;
e. policosanols: hexacosanol: from 5 mg to 15 mg/day;
f. pantethine: from 10 mg to 30 mg/day;
g. selenium: from 25 μg to 75 μg/day; and
h. zinc: from 5 mg to 15 mg/day.

21. The method according to claim 12, in which the components of the dosage are administered in unitary form, or in coordinated, sequential form.

22. The method according to claim 12, in which said components of the dosage are administered in the form of a pharmaceutical composition or a food supplement.

23. The method according to claim 12, in which said disease is selected from the group consisting of type 2 diabetes and its complications, syndrome X, polycystic ovary syndrome and obesity.

* * * * *